(12) United States Patent  
Tanaka et al.

(10) Patent No.: US 9,617,508 B2  
(45) Date of Patent: Apr. 11, 2017

(54) CULTURE CONTAINER, CULTURE OBSERVATION APPARATUS AND CULTURE OBSERVATION METHOD

(71) Applicant: Sony Corporation, Tokyo (JP)

(72) Inventors: Eiichi Tanaka, Chiba (JP); Shinsuke Haga, Tokyo (JP); Shin Hasegawa, Kanagawa (JP); Tatsuya Minakawa, Kanagawa (JP); Suguru Dowaki, Kanagawa (JP); Eriko Matsui, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/028,070

(22) Filed: Sep. 16, 2013

(65) Prior Publication Data

US 2014/0087410 A1    Mar. 27, 2014

(30) Foreign Application Priority Data

Sep. 25, 2012  (JP) ................. 2012-211480

(51) Int. Cl.
  *C12M 1/00*  (2006.01)
  *C12M 3/00*  (2006.01)
  (Continued)

(52) U.S. Cl.
  CPC ............ *C12M 41/14* (2013.01); *C12M 21/02* (2013.01); *C12M 23/12* (2013.01); *C12M 23/20* (2013.01);
  (Continued)

(58) Field of Classification Search
  CPC ...... C12M 23/12; C12M 23/04; C12M 25/06; B01L 3/50; B01L 3/52; B01L 2300/0829
  See application file for complete search history.

(56) References Cited

U.S. PATENT DOCUMENTS 4,301,252 A * 11/1981 Baker et al. ............... 435/303.1
4,786,601 A * 11/1988 Rothenberg .......... B01L 3/5085
                                                          422/942

(Continued)

FOREIGN PATENT DOCUMENTS

JP       58-155087       9/1983
JP       10-028576       2/1998

(Continued)

OTHER PUBLICATIONS http://en.wikipedia.org/wiki/Phase_contrast_microscope, 2005.*

(Continued)

*Primary Examiner* — Nathan Bowers
(74) *Attorney, Agent, or Firm* — K&L Gates LLP

(57) ABSTRACT

A culture container includes a first transparent member being capable of keeping a predetermined temperature; a second transparent member facing to the first transparent member; a housing member to which the first transparent member and the second transparent member are adhered forming a culture space being capable of housing a well plate together with the first transparent member and the second transparent member; and a sealing member for sealing a liquid injected into the culture space between the first transparent member and the housing member.

12 Claims, 22 Drawing Sheets

(51) Int. Cl.
  *B01L 3/00* (2006.01)
  *C12Q 1/02* (2006.01)
  *C12M 1/12* (2006.01)
  *C12M 1/34* (2006.01)
  *C12M 1/32* (2006.01)
  *C12Q 3/00* (2006.01)

(52) U.S. Cl.
  CPC ............ *C12M 23/22* (2013.01); *C12M 25/06* (2013.01); *C12M 29/06* (2013.01); *C12M 31/02* (2013.01); *C12M 37/04* (2013.01); *C12M 41/12* (2013.01); *C12M 41/36* (2013.01); *C12Q 1/02* (2013.01); *C12Q 3/00* (2013.01)

(56) References Cited

U.S. PATENT DOCUMENTS

| | | | | |
|---|---|---|---|---|
| 5,858,770 | A * | 1/1999 | Perlman | B01L 3/5085 435/297.5 |
| 6,008,010 | A * | 12/1999 | Greenberger et al. | 435/41 |
| 2004/0077073 | A1* | 4/2004 | Schindler et al. | 435/287.1 |
| 2005/0105172 | A1* | 5/2005 | Hasegawa et al. | 359/368 |
| 2008/0032397 | A1* | 2/2008 | Korpinen | 435/303.1 |
| 2009/0141345 | A1* | 6/2009 | Tsuchiya | 359/393 |
| 2014/0045253 | A1* | 2/2014 | Zou | 435/289.1 |

FOREIGN PATENT DOCUMENTS

| | | |
|---|---|---|
| JP | 11-337830 | 12/1999 |
| JP | 2001-125003 | 5/2001 |
| JP | 2002-286592 | 10/2002 |
| JP | 2003-302407 | 10/2003 |
| JP | 2006-000054 | 1/2006 |
| JP | 2006-238802 | 9/2006 |
| JP | 2007-108445 | 4/2007 |
| JP | 2008-505629 | 2/2008 |
| JP | 2009-201509 | 9/2009 |
| JP | 2009-296938 | 12/2009 |
| JP | 2011-521642 | 7/2011 |
| WO | 2011/094572 | 8/2011 |

OTHER PUBLICATIONS

Japanese Office Action issued Mar. 1, 2016 in corresponding Japanese Application No. 2012-211480.
Chinese Office Action issued Nov. 12, 2015 in corresponding Chinese Application No. 2013104287788.
Japanese Office Action issued Nov. 17, 2015 in corresponding Japanese Application No. 2012-211480.
Chinese Office Action issued Jul. 11, 2016 in corresponding Chinese Application No. 2013-10428778.8.

* cited by examiner

FIG.7A

| Water level | Temperature decrease amount |
|---|---|
| 13mm | 0.7°C |
| 2mm | 1.5°C |

FIG.7B

|  | Temperature decrease amount |
|---|---|
| 9.5mm | 0.4°C |

FIG.24

Measurement 1 liquid L (distance B1: 0 mm, water level B2: 4 mm)

| No. | Outer periphery | | | | | Inner periphery | | | | diff |
|---|---|---|---|---|---|---|---|---|---|---|
| | (1) | (2) | (3) | (4) | (5) | (6) | (7) | (8) | (9) | max-min |
| Well water temperature | 35 | 35 | 34.2 | 34.6 | 36.4 | 37.1 | 37.7 | 36.3 | 37.7 | 3.5 |
| Well water temperature average | 34.7 | | | | | 37.04 | | | | -2.34 |

Measurement 1-(1) liquid L (distance B1: 0 mm, water level B2: 4 mm), side heater on (37°C)

| No. | Outer periphery | | | | | Inner periphery | | | | diff |
|---|---|---|---|---|---|---|---|---|---|---|
| | (1) | (2) | (3) | (4) | (5) | (6) | (7) | (8) | (9) | max-min |
| Well water temperature | 39.2 | 39.8 | 37.8 | 38.7 | 39.1 | 39.5 | 38.8 | 39 | 38.5 | 2 |
| Well water temperature average | 38.875 | | | | | 38.98 | | | | -0.105 |

Measurement 2 liquid L (distance B1: 2 mm, water level B2: 6 mm)

| No. | Outer periphery | | | | | Inner periphery | | | | diff |
|---|---|---|---|---|---|---|---|---|---|---|
| | (1) | (2) | (3) | (4) | (5) | (6) | (7) | (8) | (9) | max-min |
| Well water temperature | 43.8 | 43 | 40.9 | 41.8 | 40.8 | 40.4 | 39.2 | 38.7 | 38.2 | 5.6 |
| Well water temperature average | 42.375 | | | | | 39.46 | | | | 2.915 |

Measurement 3 liquid L (distance B1: 9 mm, water level B2: 11 mm)

| No. | Outer periphery | | | | | Inner periphery | | | | diff |
|---|---|---|---|---|---|---|---|---|---|---|
| | (1) | (2) | (3) | (4) | (5) | (6) | (7) | (8) | (9) | max-min |
| Well water temperature | 40.8 | 40.2 | 39 | 39.3 | 37 | 38.3 | 37.2 | 38.7 | 37.4 | 4.2 |
| Well water temperature average | 39.825 | | | | | 37.3 | | | | 2.525 |

Measurement 4 no liquid L (distance B1: 0 mm)

| No. | Outer periphery | | | | | Inner periphery | | | | diff |
|---|---|---|---|---|---|---|---|---|---|---|
| | (1) | (2) | (3) | (4) | (5) | (6) | (7) | (8) | (9) | max-min |
| Well water temperature | 38.9 | 38.6 | 38.8 | 38.5 | 38.5 | 37.5 | 38 | 38 | 37 | 1.9 |
| Well water temperature average | 38.7 | | | | | 37.8 | | | | 0.9 |

Measurement 5 no liquid L (distance B1: 2 mm)

| No. | Outer periphery | | | | | Inner periphery | | | | diff |
|---|---|---|---|---|---|---|---|---|---|---|
| | (1) | (2) | (3) | (4) | (5) | (6) | (7) | (8) | (9) | max-min |
| Well water temperature | 38.4 | 38.2 | 38.3 | 38.9 | 38.2 | 36.9 | 38 | 37.3 | 37 | 2 |
| Well water temperature average | 38.45 | | | | | 37.48 | | | | 0.97 |

Measurement 6 no liquid L, skirt position: 0 mm

| No. | Outer periphery | | | | | | Inner periphery | | | diff |
|---|---|---|---|---|---|---|---|---|---|---|
| | (1) | (2) | (3) | (4) | (5) | (6) | (7) | (8) | (9) | max-min |
| Well water temperature | 38.3 | 39.3 | 38.3 | 37.4 | 36.3 | 36.7 | 35.4 | 35.8 | 35.8 | 3.9 |
| Well water temperature average | 38.325 | | | | | | 36 | | | 2.325 |

Measurement 7 no liquid L, skirt position: 2 mm

| No. | Outer periphery | | | | | | Inner periphery | | | diff |
|---|---|---|---|---|---|---|---|---|---|---|
| | (1) | (2) | (3) | (4) | (5) | (6) | (7) | (8) | (9) | max-min |
| Well water temperature | 37.2 | 36.9 | 37.2 | 37.3 | 36.7 | 36.2 | 37.2 | 37.7 | 37.2 | 1.5 |
| Well water temperature average | 37.15 | | | | | | 37 | | | 0.15 |

Measurement 8 no liquid L, skirt position: 0 mm, water level B2: 6 mm

| No. | Outer periphery | | | | | | Inner periphery | | | diff |
|---|---|---|---|---|---|---|---|---|---|---|
| | (1) | (2) | (3) | (4) | (5) | (6) | (7) | (8) | (9) | max-min |
| Well water temperature | 39 | 38.3 | 34.7 | 32.9 | 36.6 | 38.6 | 37.3 | 33.8 | 37 | 6.1 |
| Well water temperature average | 36.225 | | | | | | 36.66 | | | -0.435 |

Measurement 9 no liquid L, skirt position: 2 mm, side heater on (41°C)

| No. | Outer periphery | | | | | | Inner periphery | | | diff |
|---|---|---|---|---|---|---|---|---|---|---|
| | (1) | (2) | (3) | (4) | (5) | (6) | (7) | (8) | (9) | max-min |
| Well water temperature | 38 | 37.6 | 38.3 | 38.9 | 37.3 | 36.7 | 37.7 | 38.2 | 37.4 | 2.2 |
| Well water temperature average | 38.2 | | | | | | 37.46 | | | 0.74 |

Measurement 10 no liquid L, skirt position: 2 mm, side heater on (37°C)

| No. | Outer periphery | | | | | | Inner periphery | | | diff |
|---|---|---|---|---|---|---|---|---|---|---|
| | (1) | (2) | (3) | (4) | (5) | (6) | (7) | (8) | (9) | max-min |
| Well water temperature | 37.7 | 37.2 | 37.8 | 38.2 | 37.2 | 37.2 | 38 | 38 | 37.3 | 1 |
| Well water temperature average | 37.725 | | | | | | 37.54 | | | 0.185 |

FIG.25

CULTURE CONTAINER, CULTURE OBSERVATION APPARATUS AND CULTURE OBSERVATION METHOD

CROSS REFERENCES TO RELATED APPLICATIONS

The present application claims priority to Japanese Priority Patent Application JP 2012-211480 filed in the Japan Patent Office on Sep. 25, 2012, the entire content of which is hereby incorporated by reference.

BACKGROUND

The present disclosure relates to a culture container being capable of observing an object to be observed while culturing, a culture observation apparatus utilizing the culture container, and a culture observation method.

SUMMARY

When the object to be observed such as living cells is observed, a culture container is used to observe the object to be observed while culturing. The culture container is configured such that a temperature, a humidity, a gas (such as $CO_2$) partial pressure etc. can be adjusted in order to keep an environment suitable for culturing the object to be observed (hereinafter referred to as "culture environment"). In general, the object to be observed is housed in each well of a well plate (a plate on which a plurality of wells are disposed), and is kept under the culture environment by housing the well plate in the culture container.

Here, it is desirable that the culture container can provide the culture environment of each well as uniform as possible. If each well has a different culture environment, a growth speed etc. of the object to be observed such as cells are different, which will be unsuitable for observation. For example, Japanese Patent Application Laid-open No. 10-28576 discloses a culture container including "a transparent heat generation plate" disposed at a bottom surface of the well plate. The heat generation plate allows the bottom surface of the well plate to be heated uniformly and the culture environment to be uniform.

However, even if the heat generation plate described in Japanese Patent Application Laid-open No. 10-28576 is used, the heat generated by the heat generation plate may produce a temperature irregularity and the culture environment may be insufficiently uniform. In particular, as the heat generation plate is disposed at the bottom surface of the well plate, the heat generation plate should be transparent for observation. Moreover, a configuration of a heating element may be restricted.

Furthermore, the culture container is often open to replace the well plate, etc. In order to maintain the culture environment when the culture container is open, the heat generation plate should be controlled with a high degree of accuracy. In this case, a response etc. of the heat generation plate may be important.

It is desirable to provide a culture container, a culture observation apparatus and a culture observation method suitable for keeping a culture environment.

A culture container according to an embodiment of the present application includes a first transparent member, a second transparent member, a housing member, and a sealing member.

The first transparent member is capable of keeping a predetermined temperature.

The second transparent member faces to the first transparent member.

The housing member to which the first transparent member and the second transparent member are adhered forms a culture space being capable of housing a well plate together with the first transparent member and the second transparent member.

The sealing member seals a liquid injected into the culture space between the first transparent member and the housing member.

This configuration allows the liquid to be injected into the culture space. When the culture space is open, the culture environment (temperature, humidity) can be stably maintained by high thermal conductivity and high thermal capacity of the liquid. Also, the liquid can mitigate the temperature irregularity of the first transparent member, and it is possible to uniform the culture environment regardless of positions of the wells in the well plate.

The culture container may further include a porous member for coating a liquid level of the liquid injected into the culture space.

By this configuration, the porous member can prevent the liquid injected into the culture space from fluctuating and from entering wrongly into the wells of the well plate. On the other hand, the porous member can transmit vapor of the liquid, whereby the liquid can maintain the culture environment.

The culture container may further includes an antiscattering member adhered to the porous member for coating a gap between the well plate housed in the culture space and the porous member.

By this configuration, the antiscattering member can prevent the liquid between the porous member and the well plate from scattering.

A notch is formed on the first transparent member that forms a gap between the first transparent member and the well plate disposed on the first transparent member.

This configuration allows the liquid to be easily penetrated between the well plate and the first transparent member after the well plate is mounted on the first transparent member and the liquid is injected into the culture space.

The culture container may further include a support member made of a thermal insulation material for supporting the well plate housed in the culture space.

This configuration can prevent the well plate from contacting with the first transparent member, and can also prevent an effect of the temperature irregularity in the first transparent member.

The first transparent member includes a transparent plate having an optical transparency, a pair of electrodes formed on the transparent plate per segment of the transparent plate, and a transparent conductive film formed on the transparent plate and connected to the pair of electrode per segment of the transparent plate.

This configuration allows the temperature (heat generation) of the first transparent member to be controlled per segment, and can prevent a generation of the temperature irregularity in the first transparent member.

A culture observation apparatus according to an embodiment of the present application includes a culture container, an illumination optical system, and a microscope optical system.

The culture container includes a first transparent member being capable of keeping a predetermined temperature, a second transparent member facing to the first transparent member, a housing member to which the first transparent member and the second transparent member are adhered, and forms a culture space being capable of housing the well plate together with the first transparent member and the second transparent member and a sealing member for sealing a liquid injected into the culture space between the first transparent member and the housing member.

The illumination optical system irradiates the culture container with an illumination light.

The microscope optical system generates a phase difference image from the illumination light irradiated from the illumination optical system and transmitted through the culture container.

By this configuration, the phase difference image of the objects to be observed can be observed using the above-described culture container.

The culture observation apparatus may further include a blower blowing air to the first transparent member.

By this configuration, air is blown to the first transparent member to change a temperature gradient of the first transparent member from a plane direction of the first transparent member to a thickness direction of the first transparent member, thereby avoiding the temperature irregularity in the plane direction of the first transparent member. In addition, air is blown by this configuration at the same time when a top cover of the culture container is closed, thereby suppressing a temperature increase of culture media in the well plate.

The first transparent member may include an infrared absorbing material.

The illumination optical system irradiates the second transparent member with an illuminated light and infrared rays.

By this configuration, the infrared rays are irradiated to heat the second transparent member with a high response. In addition, by adjusting the distance between the lenses in the illumination optical system, an intensity distribution of the illuminated light on the second transparent member can be adjusted, thereby adjusting the temperature distribution.

The illumination optical system may include a draw ring having a ring-shaped slit and an infrared illumination unit disposed at the culture container side of the ring-shaped slit and at an inner periphery of the ring-shaped slit.

By this configuration, the well plate can be irradiated with the infrared rays without blocking the illuminated light.

A culture observation method includes preparing a culture container including a first transparent member being capable of keeping a predetermined temperature, a second transparent member facing to the first transparent member, a housing member to which the first transparent member and the second transparent member are adhered, and forms a culture space being capable of housing the well plate together with the first transparent member and the second transparent member and a sealing member for sealing a liquid injected into the culture space between the first transparent member and the housing member;

housing the well plate in which an object to be observed is housed into the culture space;

injecting a liquid into the culture space; and keeping the culture space to a culture environment of the object to be observed.

By this method, the object to be observed can be observed while the culture environment is stably maintained.

As described above, according to the embodiments of the present application, there are provided a culture container, a culture observation apparatus and a culture observation method suitable for keeping the culture environment.

These and other objects, features and advantages of the present disclosure will become more apparent in light of the following detailed description of best mode embodiments thereof, as illustrated in the accompanying drawings.

Additional features and advantages are described herein, and will be apparent from the following Detailed Description and the figures.

BRIEF DESCRIPTION OF THE FIGURES

FIGS. 7A and 7B are each a table showing a liquid level of a liquid in the culture container according to the first embodiment and a temperature decrease amount of the object to be observed;

FIG. 24 is a table showing measured values according to embodiments;

FIG. 25 is a table showing measured values according to embodiments; and

DETAILED DESCRIPTION

Hereinafter, an embodiment of the present disclosure will be described with reference to the drawings.

(First Embodiment)

A culture observation apparatus and a culture container according to a first embodiment will be described.

[Configuration of Culture Observation Apparatus]

Figure 1:
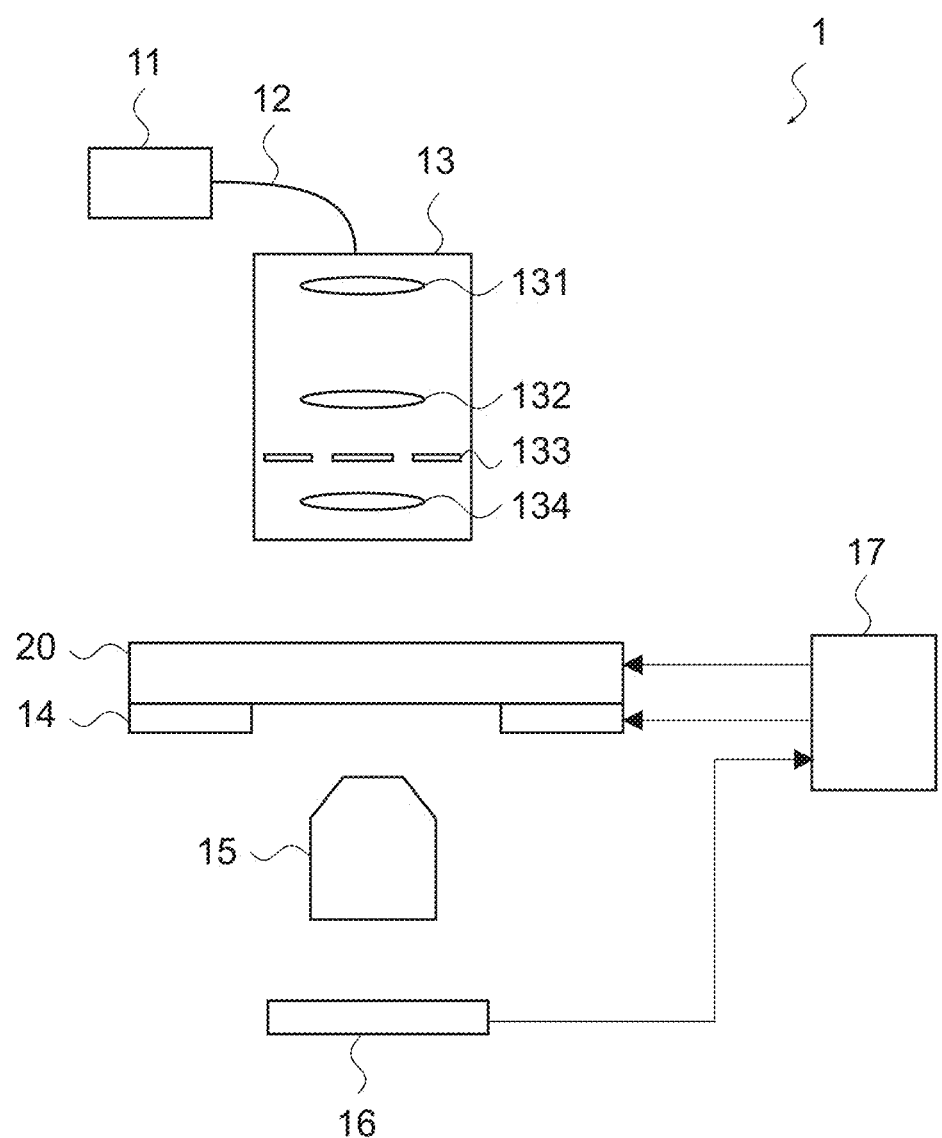
FIG. 1 is a schematic diagram of a culture observation apparatus according to a first embodiment.

FIG. 1 is a schematic diagram of a culture observation apparatus 1 according to the first embodiment. As shown in FIG. 1, the culture observation apparatus 1 includes an illumination light source 11, optical fibers 12, an illumination optical system 13, a stage 14, a microscope optical system 15, an image capture sensor 16 and a control unit 17. At the stage 14, a culture container 20 in which objects to be observed (cells etc.) are housed is mounted. The culture observation apparatus 1 can be a phase difference microscope that can capture a phase difference image of objects to be observed (cells etc.).

The illumination light source 11 can be any light source such as a halogen lamp. The illumination light source 11 can be controlled by the control unit 17 so as to control a light emission timing. The optical fibers 12 transmit an illuminated light irradiated from the illumination light source 11 to the illumination optical system 13. Any optical fibers 12 can be used.

The illumination optical system 13 adjusts the illuminated light transmitted from the optical fibers 12 to provide a uniform illuminated light suitable to form the phase difference image. The illumination optical system 13 can have a first lens 131, a second lens 132, a draw ring 133 and a condenser lens 134. The first and second lenses 131 and 132 may be field lenses generally used in the illumination optical system. The draw ring 133 is a plate-like member having ring-shaped slits, which will be described later, and focuses narrowly an illuminated light passed through the first and second lenses 131 and 132. The condenser lens 134 is a lens for collecting the illuminated light passed through the draw ring 133 to the object to be observed.

The stage 14 supports the culture container 20, and adjusts a position of the culture container 20. Desirably, the stage 14 may be moved in a vertical direction (a direction along an optical axis) and a horizontal direction (a direction vertical to the optical axis) by a motor etc. The stage 14 can be drive-controlled by the control unit 17, and can move the culture container 20.

The microscope optical system 15 forms the phase difference image from a light irradiated from the illumination optical system 13, and transmitted through the culture container 20 (and the objects to be observed housed therein). The microscope optical system 15 can have an objective lens, a phase difference plate, an image-forming lens and so on (not shown).

The image capture sensor 16 captures the phase difference image of the objects to be observed. The phase difference image is formed by the microscope optical system 15. The image capture sensor 16 can be a CCD (Charge Coupled Device) image sensor or a CMOS (Complementary Metal Oxide Semiconductor) image sensor. An output from the image capture sensor 16 will be provided to the control unit 17.

The control unit 17 is, for example, an information processing apparatus, provides a control signal to the stage 14 or other configuration, controls an image capture of the object to be observed, and generates the phase difference image from the output from the image capture sensor 16. In addition, the control unit 17 can acquire information about an environment (temperature etc.) of the culture container 20, and control the environment, which will be described later.

The culture observation apparatus 1 has the above-described configuration. The above-described configuration of the culture observation apparatus 1 is only illustrative, and can be changed. For example, the culture observation apparatus 1 may have an eye lens etc. for observing the objects to be observed by human's eyes instead of the image capture sensor 16.

[Configuration of Culture Container]

Figure 2A:
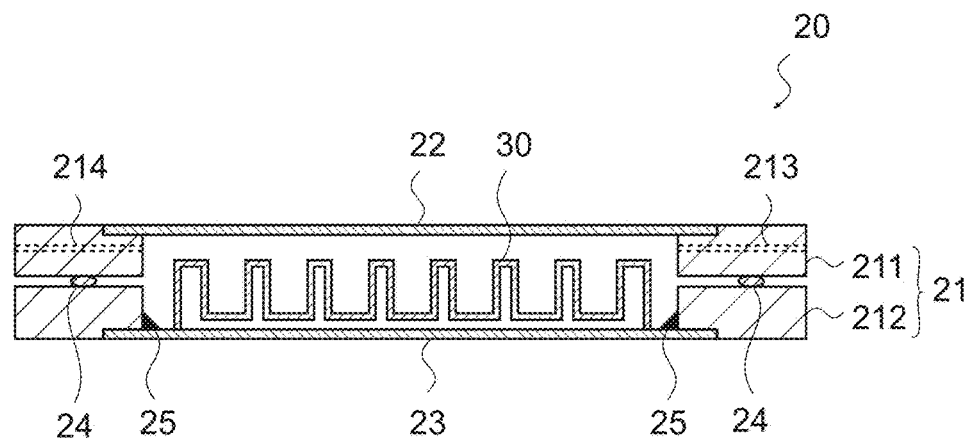
FIGS. 2A and 2B are each a schematic diagram of a culture container according to the first embodiment.
Figure 2B:
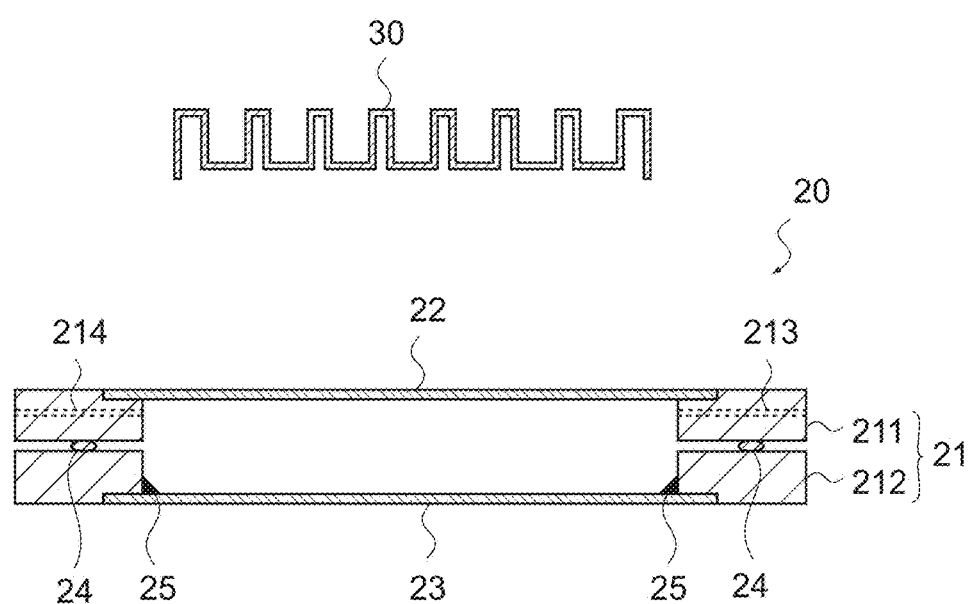

A culture container 20 that can be used in the above-described culture observation apparatus 1 will be described. FIGS. 2A and 2B are each a schematic diagram of the culture container 20. The culture container 20 is configured so that a well plate 30 can be housed inside of the culture container 20. FIG. 2A shows the culture container 20 in which the well plate 30 is housed. FIG. 2B shows the well plate 30 and culture container 2 separately.

As shown in FIGS. 2A and 2B, the culture container 20 has a housing member 21, a first transparent member 23, a second transparent member 22, a sealing ring 24 and a water proof member 25. The housing member 21, the first transparent member 23 and the second transparent member 22 form a space (a culture space).

The housing member 21 form the culture space together with the first transparent member 23 and the second transparent member 22. The shape of the housing member 21 is not especially limited, but can have a cylindrical shape or a cuboid shape. The material of the housing member 21 is not especially limited, but can be a synthetic resin and the like.

The housing member 21 may include a cover 211 and a main body 212. The cover 211 is open to or closed from the body, whereby the well plate 30 can be replaced. The cover 211 and the main body 212 can be open and closed by a hinge (not shown), for example. The cover 211 has an opening for fitting the second transparent member 22 thereinto, and the main body 212 has an opening for fitting the first transparent member 23 thereinto.

The cover 211 has a gas supply hole 213 and a gas exhaust hole 214. The gas supply hole 213 is connected to a gas source (a gas cylinder etc.), and can supply a predetermined gas (for example, carbon dioxide) to the culture space. The gas exhaust hole 214 can exhaust the gas within the culture space. The gas supply hole 213 and the gas exhaust hole 214 can be closed when they are not in use.

The first transparent member 23 is fitted into the opening of the main body 212 to form a bottom surface of the culture space. Onto the first transparent member 23, the well plate 30 housed in the culture space is mounted. The first transparent member 23 can be made of an optically transparent material such as glass and a synthetic resin. It is suitable that a size of the first transparent member 23 is such that the first transparent member 23 faces almost all or all of the well plate 30 in order that the illuminated light transmitted through the well plate 30 (and the objects to be observed housed therein) reaches the microscope optical system 15.

Figure 3:
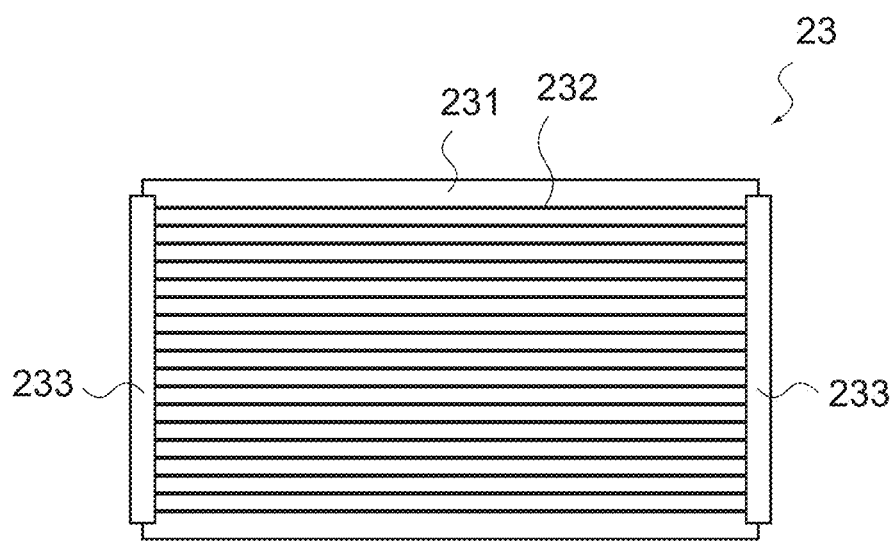
FIG. 3 is a schematic diagram of a first transparent member of the culture container.

The first transparent member 23 can be a heater for keeping a predetermined temperature. FIG. 3 is a schematic diagram showing the first transparent member 23. As shown in FIG. 3, the first transparent member 23 includes a transparent plate 231 having an optical transparency and a transparent conductive film 232 formed thereon. The transparent conductive film 232 is connected to electrodes 233, and generates heat by an electricity supply from the electrodes 233. The first transparent member 23 is not limited to such a configuration. It is suitable that the first transparent member 23 can heat and generate electricity uniformly (without irregularity) in-plane thereof as long as the first transparent member 23 has an optical transparency and can generate electricity.

The second transparent member 22 is fitted into the opening of the cover 211 to face the first transparent member 23. The second transparent member 22 can be made of an optically transparent material such as glass and a synthetic resin. It is suitable that a size of the second transparent member 22 is such that the second transparent member 22 faces almost all or all of the well plate 30 in order that the illuminated light irradiated from the illumination optical system 13 reach the well plate 30 (and the objects to be observed housed therein). The second transparent member 22 can be a heater for keeping a predetermined temperature similar to the first transparent member 23.

The sealing ring 24 is disposed between the cover 211 and the main body 212 of the housing member 21, and seals the culture space therebetween. The sealing ring 24 can be an annular member made of an elastic material such as rubber.

The waterproof member 25 can prevent a liquid (as described later) from leaking between the first transparent member 23 and the main body 212. The waterproof member 25 may be a synthetic resin that is applied to a joint between the first transparent member 23 and the body part 212 after the first transparent member 23 is fitted into the main body 212. Alternatively, the waterproof member 25 can have other configurations that can prevent the liquid leakage between the first transparent member 23 and the main body 212.

[Well Plate]

Figure 4A:
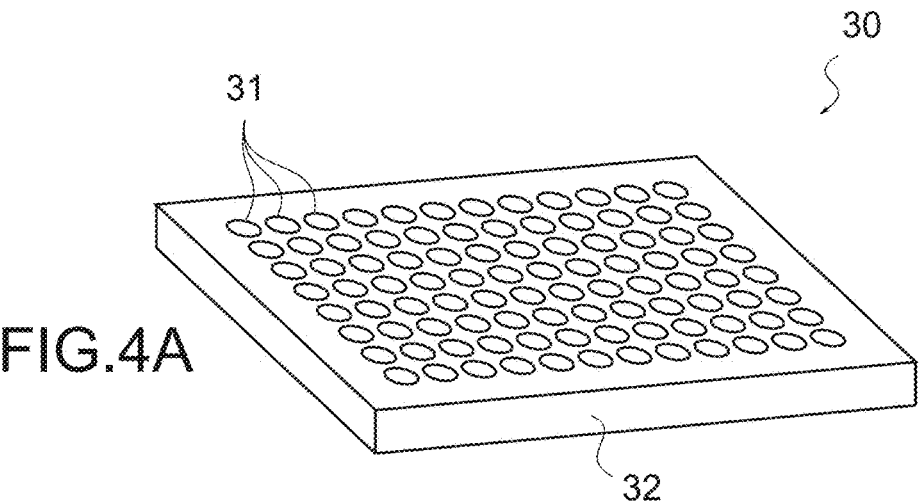
FIGS. 4A, 4B and 4C are each a schematic diagram of well plate housed in the culture container.
Figure 4B:
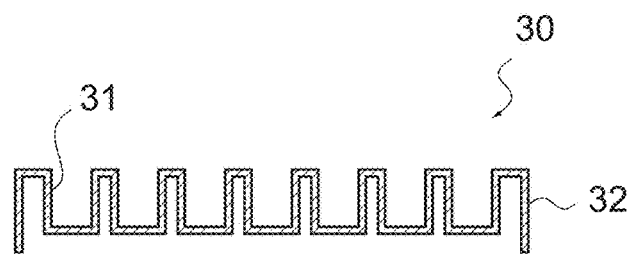
Figure 4C:
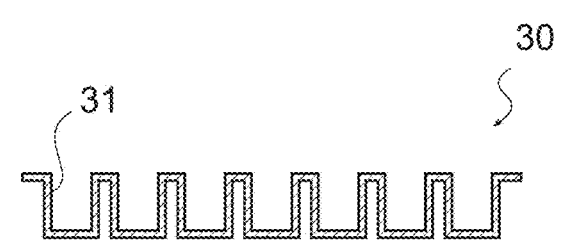

A well plate 30 housed in the culture space will be described. The well plate 30 may be commercially available. FIGS. 4A, 4B and 4C are each a schematic diagram of well plate housed in the culture container. FIG. 4A is a perspective view of the well plate 30. FIG. 4B is a sectional view of the well plate 30. As shown in FIG. 4B, the well plate 30 has a plurality of wells 31 two-dimensionally arranged. Each well 31 has the same pore diameter and depth, and can house the object to be observed (cells etc.). Also, each well 31 can house a culture liquid of cells together with the object to be observed.

In the well plate 30, a skirt 32 is disposed around the wells 31. The skirt 32 is formed longer (higher) than a depth of each well 31 so that a bottom surface of the well 31 is spaced from a mounting surface of the well plate 30.

The well plate 30 may have no skirt 32. FIG. 4C is a schematic diagram showing the well plate 30 having no skirt 32. In this case, the bottom surface of each well 31 comes into contact with the mounting surface of the well plate 30.

In the first embodiment, the well plate 30 with or without the skirt 32 can be used. The well plate 30 is housed in the culture container 20 and is then mounted on the first transparent member 23. When the well plate 30 has the skirt 32, the bottom surfaces of the wells 31 are spaced from the first transparent member 23. When the well plate 30 has no skirt 32, the bottom surfaces of the wells 31 come into contact with the first transparent member 23.

[Used Configuration of Culture Container]

Figure 5:
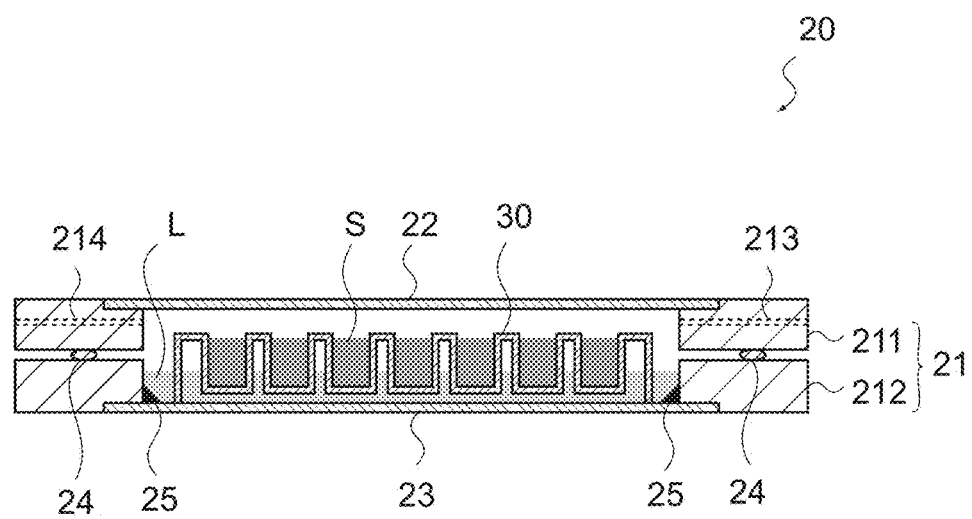
FIG. 5 is a schematic diagram showing a used configuration of the culture container.

A used configuration of the culture container 20 having the above-described configuration will be described. FIG. 5 is a schematic diagram showing the used configuration of the culture container.

As shown in FIG. 5, in the culture space of the culture container 20, a liquid L is housed together with the well plate 30. In each well 31 of the well plate 30, an object to be observed S (culture media including cells etc.) is housed. As the liquid L, a liquid having high thermal conductivity such as water is desirable. In particular, in order to prevent a generation of air bubbles, distilled water degassed by a degasifier is desirable. An amount of the liquid L is desirably such that the liquid L fills around each well 31 of the well plate 30, as shown in FIG. 5, which will be described later.

[Effects of Embodiment]

Effects of the culture container 20 according to the first embodiment will be described. As a comparison, a culture container where no liquid L is injected into a culture space (hereinafter referred to as a culture container α) is used.

A culture environment change in the culture container α is confirmed as follows: The culture container α houses a thermal chamber (25° C.) capable of keeping temperature and humidity. Also, a sensor for measuring temperature and humidity is disposed within the culture container α. Based on outputs from the sensor, heaters disposed on the culture container α and a stage are feedback-controlled.

Figure 6:
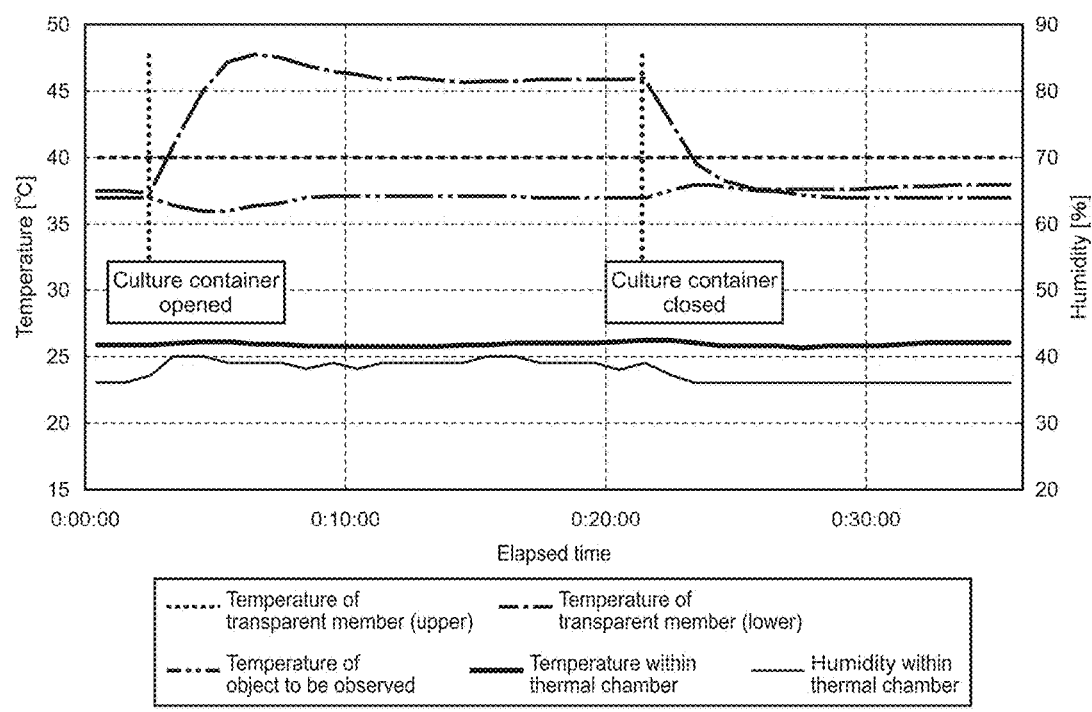
FIG. 6 is a graph showing a change in temperature of each heater disposed on a culture container according to a comparative embodiment and an object to be observed.

FIG. 6 is a graph showing a change in temperature of each heater (each transparent member) disposed on the culture container α and an object to be observed when the culture container α is open. Open of the culture container α means that the cover 211 is open to the main body 212 as for the culture container 20 according to the first embodiment, and supposes that the culture container α is open for replacing the well plate 30.

As shown in FIG. 6, when the culture space of the culture container α is kept under predetermined conditions (temperature of 37° C.) and the culture container α is open, the temperature of the culture space decreases. In order to keep the culture environment, each heater generates more heat. However, heating by the heater is not caught up with a change of the culture environment (temperature decrease). The temperature of the object to be observed is temporarily decreased by 1.5° C. Similarly, the culture container α is closed, the temperature of each heater cannot be decreased at once. Accordingly, the temperature of the object to be observed is temporarily increased.

Thus, the culture container α according to a comparative embodiment cannot follow the change in the culture environment, even if each heater is feedback-controlled. The object to be observed may be affected by the change in the culture environment. If the cells that are the object to be observed are damaged, a later observation will be significantly impacted.

In contrast, the culture container 20 according to the first embodiment inhibits the change in the culture environment by injecting the liquid L into the culture space. FIGS. 7A and 7B are each a table showing a liquid level of the liquid L and a temperature decrease amount of the object to be observed housed in the wells 31. FIG. 7A shows the temperature decrease amount of the well plate having the skirt 32 (see FIG. 4A). FIG. 7B shows the temperature decrease amount of the well plate having no skirt 32. In the well plate 30 in FIG. 7A, a distance between the bottom surface of each well 31 and the first transparent member 23 is 7 mm. In the well plate 30 in FIG. 7B, the distance is 0 mm (comes in contact with each other).

FIGS. 7A and 7B reveal that the temperature decrease amount of the object to be observed is decreased by the liquid L. They also reveal that the shorter the bottom surface of each well 31 and the first transparent member 23 are and the higher the liquid level of the liquid L is, the smaller the temperature decrease amount is. Thus, the object to be observed will not be damaged by the change in the culture environment, i.e., it is possible to keep the object to be observed to right conditions for observation.

In this way, in the culture container 20 according to the first embodiment, the liquid L can be injected into the culture space. By high thermal conductivity of the liquid L injected into the culture space, it is possible to inhibit a variation of the culture environment when the culture container α is open.

(Second Embodiment)
[Configuration of Culture Container]

Figure 8:
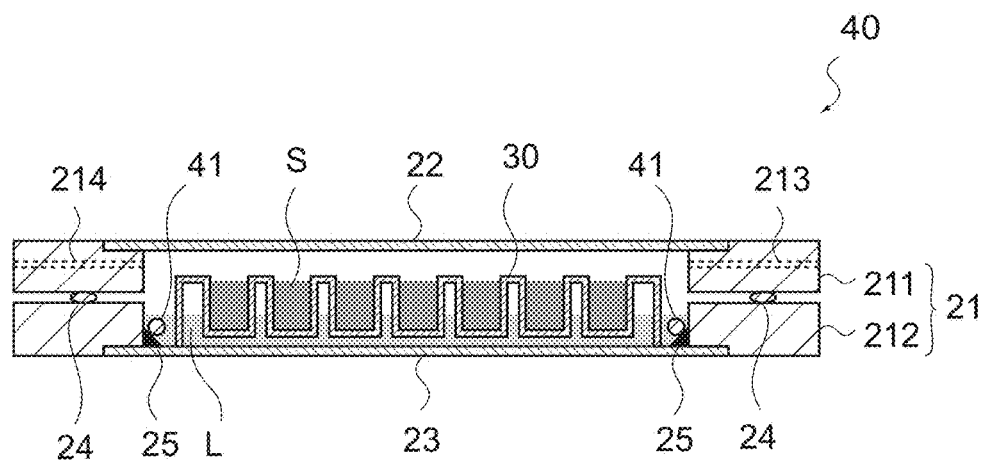
FIG. 8 is a schematic diagram of a culture container according to a second embodiment.

A culture container according to a second embodiment will be described. The culture observation apparatus is similar to the first embodiment. FIG. 8 is a schematic diagram of a culture container 40 according to the second embodiment.

As shown in FIG. 8, the culture container 40 according to the second embodiment has a side heater 41 in addition to the housing member 21, the first transparent member 23, the second transparent member 22, the sealing ring 24 and the water proof member 25 similar to the first embodiment. Into the culture space, the liquid L is injected as in the first embodiment.

The side heater 41 is a circular heater disposed around the well plate 30 when the well plate 30 is housed in the culture space. The side heater 41 may be a ribbon heater or a rubber heater. The side heater 41 is set to a predetermined temperature (for example, at 37° C.) by the control unit 17 (see FIG. 1).

In the first embodiment, the liquid L is injected into the culture space, whereby a variation of the culture environment is inhibited when the culture container 20 is open. In the second embodiment, it is possible to uniform the culture environment in an in-plane of the well plate 30.

Specifically, in each well 31 of the well plate 30, a temperature of an outer periphery (a circumferential part) of each well 31 may be lowered than a temperature of an inner periphery (a center part) of each well 31. It would appear that the first transparent member 23 generates heat, the heat flows to the other ends of the electrode, and a temperature distribution generated is directly transmitted to the wells 31. According to the second embodiment, by heating the outer periphery of the well plate 30 with the side heater 41, a decrease in the temperature of the outer periphery in the wells 31 can be prevented and a temperature difference between the inner periphery and the outer periphery of the wells can be inhibited (see Example). In this test, the first transparent member 23 having a size similar to the well plate 30 was used. When the first transparent member 23 has a larger outer diameter and the well plate 30 is disposed on the center part having a flat temperature distribution, a temperature distribution of the first transparent member 23 does not affect the well plate 30. Once the culture media (contained in the object to be observed S) in the wells 31 is vaporized, the temperature of the outer periphery becomes higher than that of the inner periphery. Such an effect is noticeable. By injecting the liquid L into the peripheries of the well plate 30, once the liquid L is vaporized, the inner and outer peripheries of the well plate 30 are humidified to an almost same vaporization degree. Thus, the temperature difference between the inner and outer peripheries can be suppressed (see FIG. 26).

(Third Embodiment)
[Configuration of Culture Container]

Figure 9:
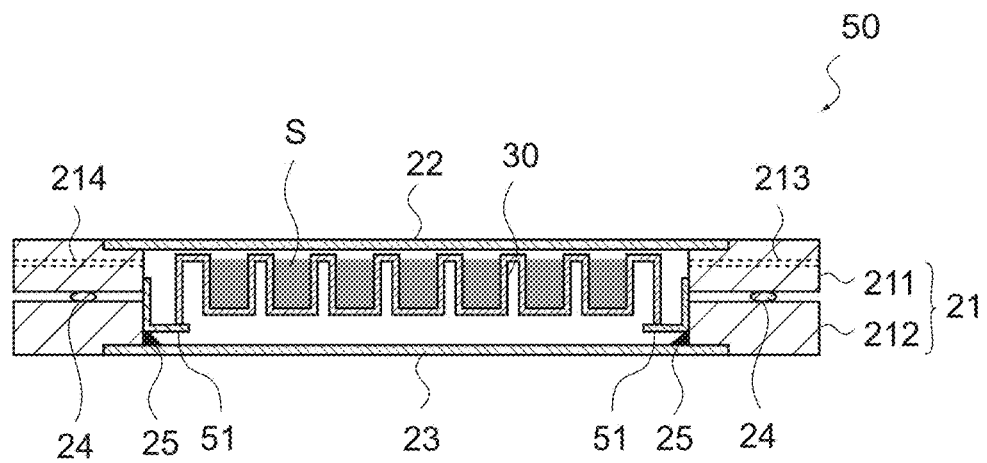
FIG. 9 is a schematic diagram of a culture container according to a third embodiment.

A culture container according to a third embodiment will be described. The culture observation apparatus is similar to the first embodiment. FIG. 9 is a schematic diagram of a culture container 50 according to the third embodiment.

As shown in FIG. 9, the culture container 50 according to the third embodiment has a well plate support member 51 in addition to the housing member 21, the first transparent member 23, the second transparent member 22, the sealing ring 24 and the water proof member 25 similar to the first embodiment. Unlike the first embodiment, the liquid L is not injected into the culture space.

The well plate support member 51 is adhered to the main body 212, and can support the well plate 30 separated from the first transparent member 23. The well plate support member 51 can be made of a material having a high thermal insulation property.

The well plate support member 51 prevents the well plate 30 from coming into contact with the first transparent member 23, whereby irregular thermal conduction from the first transparent member 23 to the skirt 32 can be inhibited. It is thus possible to suppress the temperature difference between the inner periphery and the outer periphery of the wells 31 in the well plate 30. In this case, as there is no liquid L, an optical distance between the microscope optical system 15 and the object to be observed S will not form an issue.

(Fourth Embodiment)
[Configuration of Culture Container]

Figure 10A:
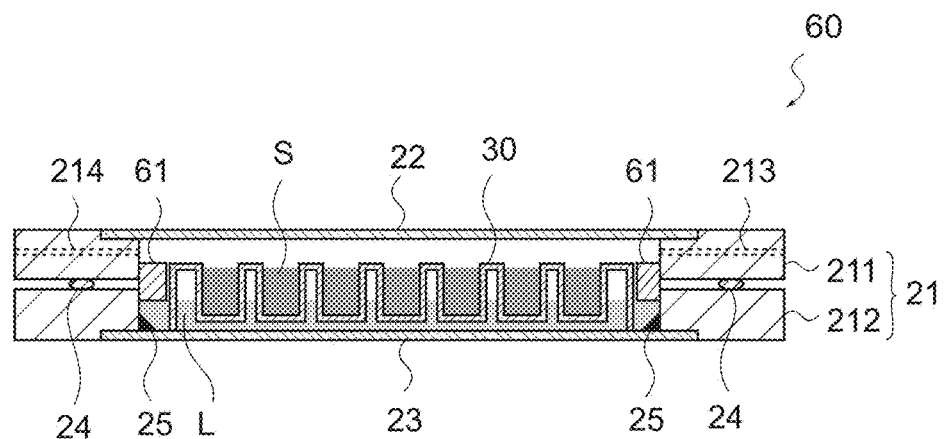
FIGS. 10A and 10B are each a schematic diagram of a culture container according to a fourth embodiment.
Figure 10B:
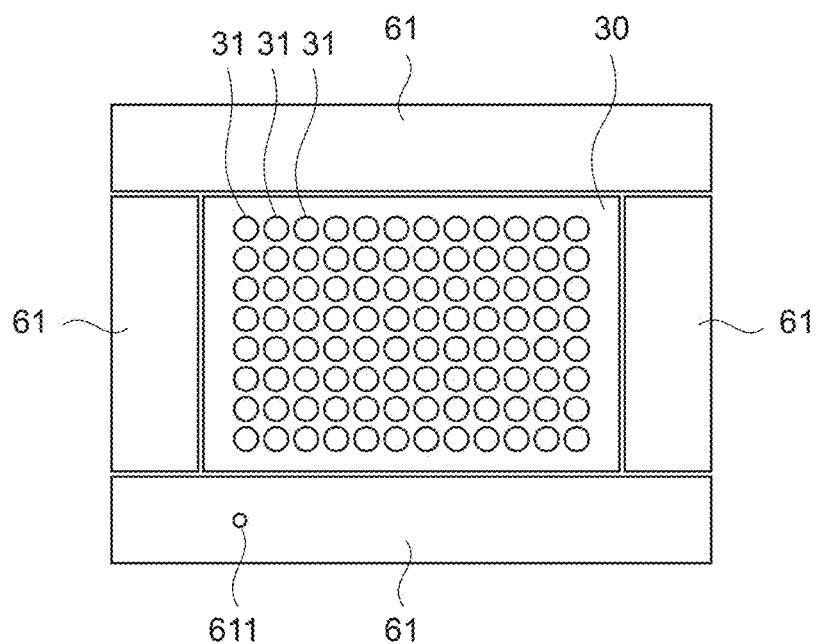

A culture container according to a fourth embodiment will be described. The culture observation apparatus is similar to the first embodiment. FIGS. 10A and 10B are each a schematic diagram of a culture container 60 according to the fourth embodiment. FIG. 10A is a cross-sectional view of the culture container 60. FIG. 10B is a plan view of a part configuration of the culture container 60.

As shown in FIGS. 10A and 10B, the culture container 60 according to the fourth embodiment has a porous member 61 in addition to the housing member 21, the first transparent member 23, the second transparent member 22, the sealing ring 24 and the water proof member 25 similar to the first embodiment Like the first embodiment, the liquid L is injected into the culture space.

The porous member 61 is a porous material, for example, a member of a humidity control building material, and is disposed to come into contact with a liquid level of the liquid L. The porous member 61 may be adhered to the main body 212 or may float at the liquid level of the liquid L.

An injection hole 611 for injecting the liquid L may be disposed on the porous member 61. It is thus possible to inject the liquid L using the injection hole 611 after the porous member 61 is disposed.

The porous member 61 provides the following benefits. Specifically, the culture container 60 moves as the stage 14 is driven as described above. By this movement, the liquid level L would be waved, and the liquid L may be undesirably introduced into the wells 31. According to the fourth embodiment, the liquid level L is coated with the porous member 61, thereby preventing the liquid L from introducing into the wells 31. In addition, the porous member 61 can transmit vapor of the liquid L due to its porosity. As a result, the liquid L can still exert a benefit that a change of the culture environment is inhibited.

Figure 11A:
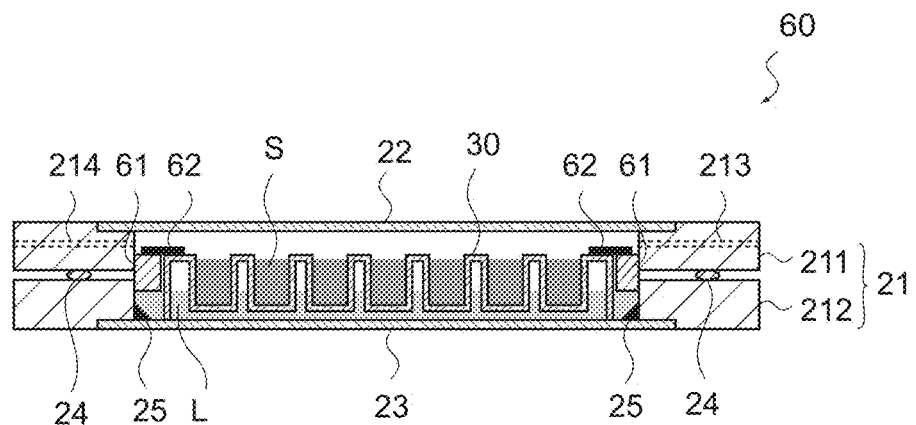
FIGS. 11A and 11B are each a schematic diagram of a culture container according to the fourth embodiment.
Figure 11B:
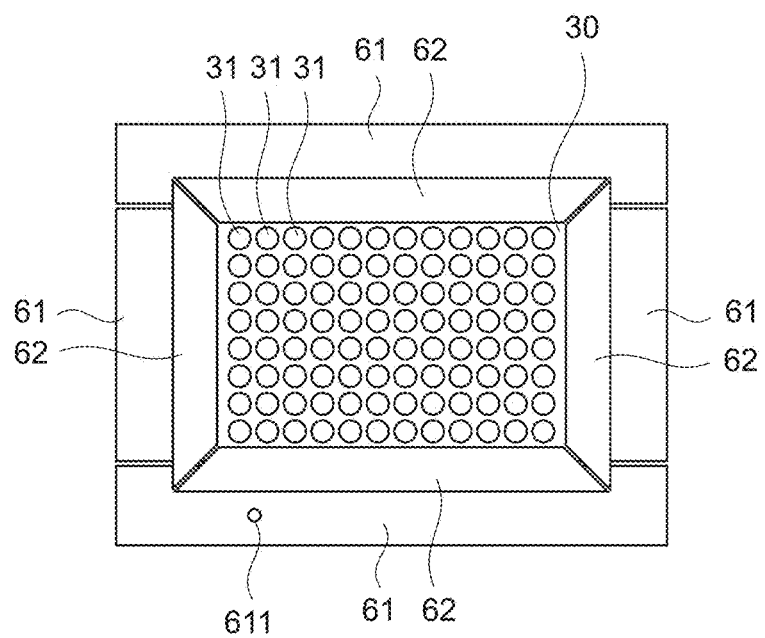

The culture container 60 may have an antiscattering member 62 in addition to the porous member 61. FIGS. 11A and 11B are each a schematic diagram of the culture container 60 having the antiscattering member 62. FIG. 11A is a cross-sectional view of the culture container 60. FIG. 11B is a plan view of a part configuration of the culture container 60.

As shown in FIGS. 11A and 11B, the antiscattering member 62 is adhered to the porous member 61, and is disposed to coat the circumferential part of the well plate 30. The antiscattering member 62 can be a flexible material, for example, a rubber sheet. The antiscattering member 62 can prevent the liquid L from scattering between the porous member 61 and the well plate 30 and from undesirably introducing into the wells 31.

(Fifth Embodiment)
[Configuration of Culture Container]

Figure 12A:
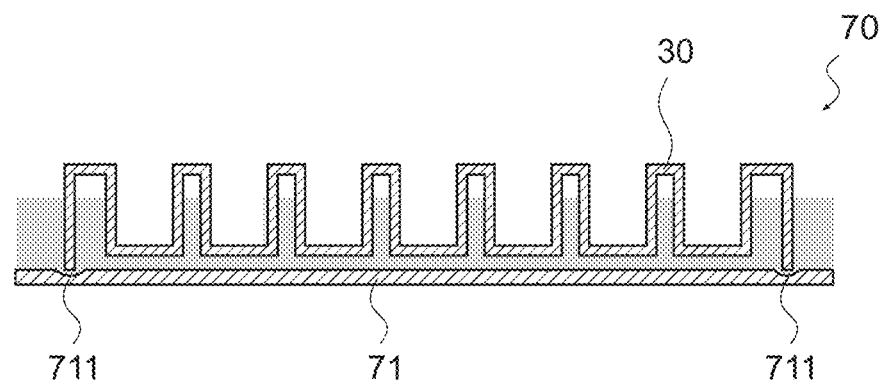
FIGS. 12A and 12B are each a schematic diagram of a culture container according to a fifth embodiment.
Figure 12B:
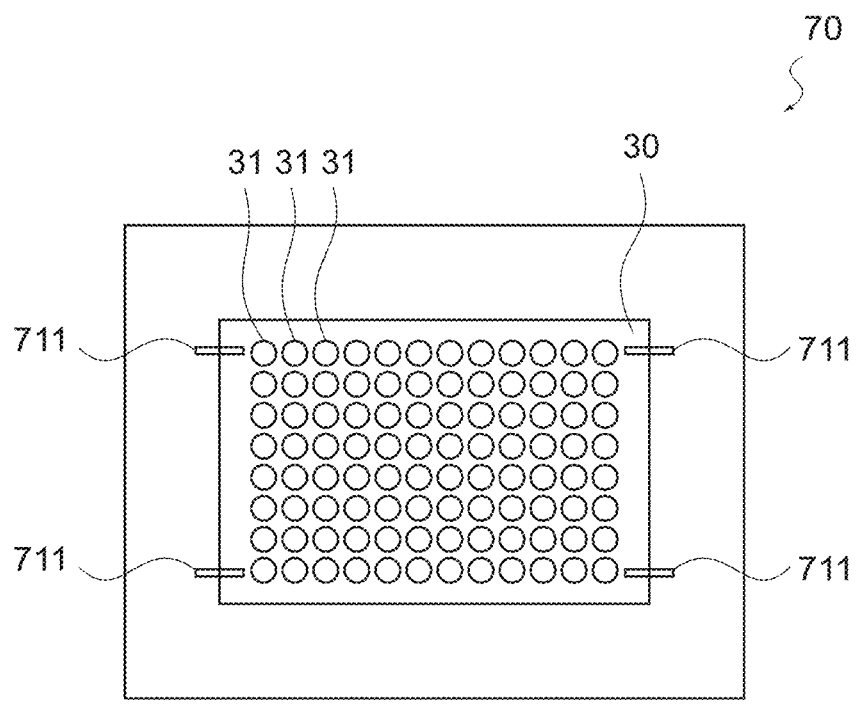

A culture container according to a fifth embodiment will be described. The culture observation apparatus is similar to the first embodiment. FIGS. 12A and 12B are each a schematic diagram of a culture container according to a fifth embodiment. FIG. 12A is a cross-sectional view of a culture container 70. FIG. 12B is a plan view of a part configuration of the culture container 70.

The culture container 70 according to the fifth embodiment has the housing member 21, the second transparent member 22, the sealing ring 24 and the water proof member 25 similar to the first embodiment (see FIG. 5). As shown in FIGS. 12A and 12B, a first transparent member 71 has a configuration different from the second transparent member 22. The first transparent member 71 has notches 711.

The notches 711 are formed in the first transparent member 71 at positions where the skirt 32 of the well plate 30 comes into contact. In the FIGS. 12A and 12B, the notches 711 are disposed at four points, but are not limited thereto. The notches 711 allows the liquid L to flow between the well plate 30 and the first transparent member 71, even if the liquid L is injected after the well plate 30 is disposed.

(Sixth Embodiment)
[Configuration of Culture Container]

Figure 13:
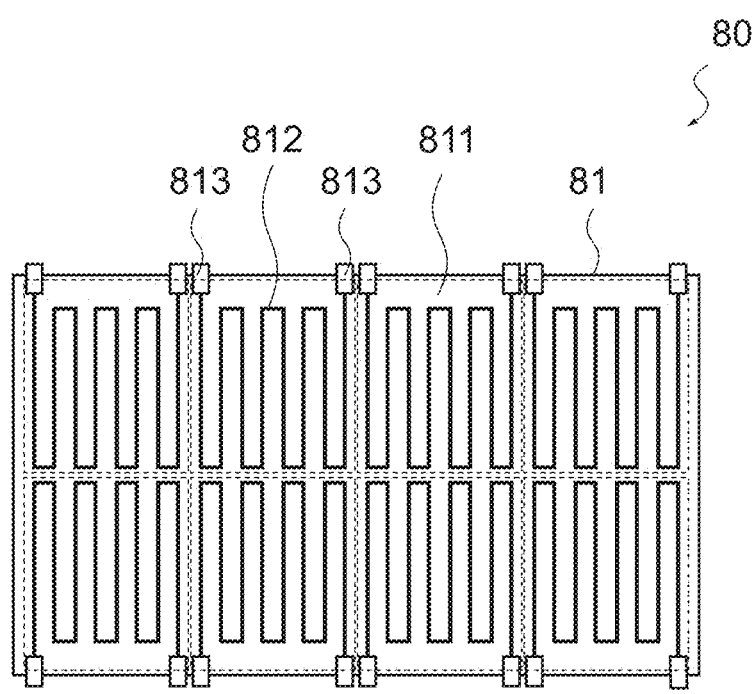
FIG. 13 is a schematic diagram of a culture container according to a sixth embodiment.

A culture container according to a sixth embodiment will be described. The culture observation apparatus is similar to the first embodiment. A culture container 80 according to the sixth embodiment has the housing member 21, the second transparent member 22, the sealing ring 24 and the water proof member 25 similar to the first embodiment (see FIG. 5). A second transparent member 81 has a configuration different from the second transparent member 22. FIG. 13 is a schematic diagram of the second transparent member 81 of the culture container 80 according to a sixth embodiment.

As shown in FIG. 13, the second transparent member 81 includes a transparent plate 811 having an optical transparency, and transparent conductive films 812 formed per segment of the transparent plate 811 (shown by dashed lines) unlike the first transparent member 23 (see FIG. 3) according to the first embodiment. The transparent conductive films 812 formed in respective segments are connected to respective pairs of electrodes 813 per respective segments, and generate heat by an electricity supply from the electrodes 813. Such a configuration of the second transparent member 81 allows a heat generation temperature to be adjusted per segment. Also, in terms of a heat generation temperature of the first transparent member 23, the culture environment (temperature) in each well 31 of the well plate 30 can be uniform. In particular, a temperature sensor (not shown) may be disposed in each well 31 per segment, and be feed-back controlled per segment.

(Seventh Embodiment)
[Configuration of Culture Container]

Figure 14:
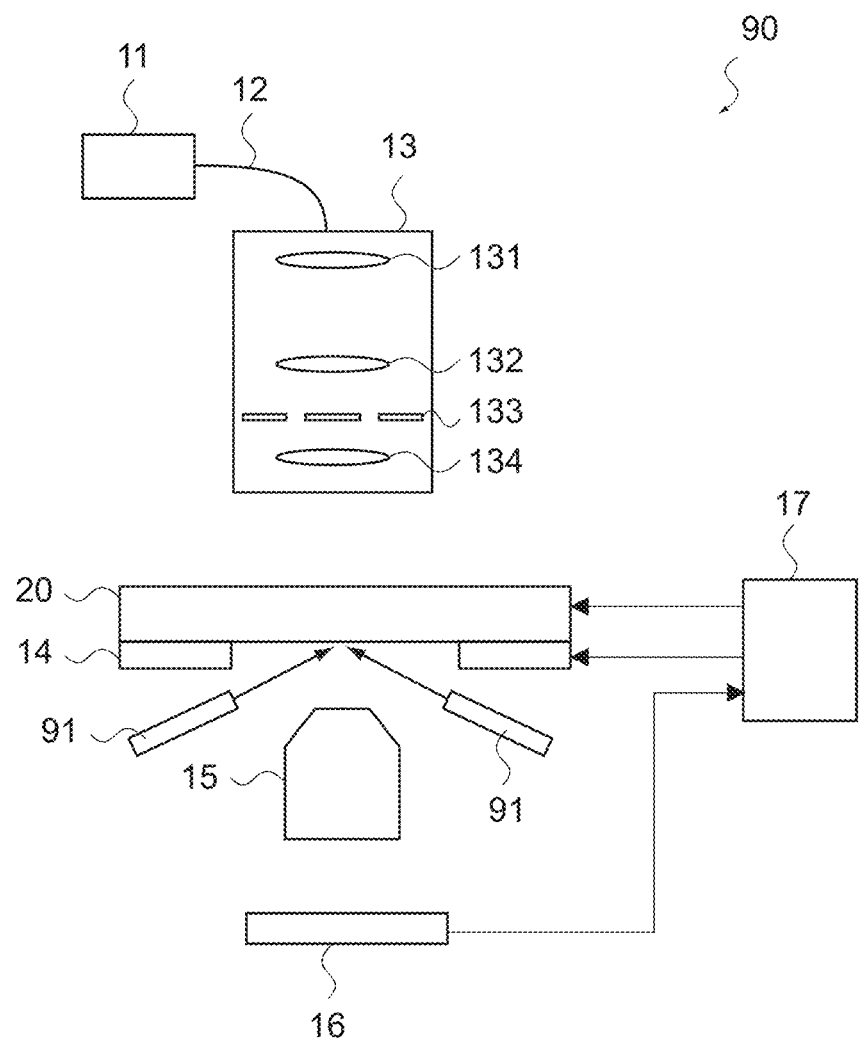
FIG. 14 is a schematic diagram of a culture observation apparatus according to a seventh embodiment.

A culture observation apparatus according to a seventh embodiment will be described. FIG. 14 is a schematic diagram of a culture observation apparatus 90 according to a seventh embodiment. As shown in FIG. 14, the culture observation apparatus 90 includes the illumination light source 11, the optical fibers 12, the illumination optical system 13, the stage 14, the microscope optical system 15, the image capture sensor 16 and the control unit 17 similar to the culture observation apparatus 1 according to the first embodiment. The culture observation apparatus 90 further includes blowers 91 in addition to the above-described constituents. To the culture observation apparatus 90, any of the culture containers shown in the first to sixth embodiments may be set. Here, the culture container 20 according to the first embodiment will be described as an example.

As shown in FIG. 14, the blowers 91 blow air to the first transparent member 23 of the culture container 20 around the microscope optical system 15. Each blower 91 may be a nozzle connected to a gas source such as a gas cylinder, or may be a blower equipped with a fan. As shown in FIG. 14, two blowers 91 are disposed across the microscope optical system 15, but one or more blowers 91 may be disposed.

Figure 15A:
FIGS. 15A and 15B are each a schematic diagram showing a temperature distribution in the first transparent member of the culture observation apparatus.
Figure 15B:

When the blowers 91 blow air to the first transparent member 23, the heat generation temperature of the first transparent member 23 can be uniform. FIGS. 15A and 15B are each a schematic diagram showing a temperature distribution in the first transparent member 23. FIG. 15A shows a temperature distribution when the blowers 91 do not blow air. FIG. 15B shows a temperature distribution when the blowers 91 blow air.

As shown in FIG. 15A, when no blower 91 is disposed, there is a temperature difference between a center part and a circumferential part in the first transparent member 23. This is because heat flows along a plane direction (a direction perpendicular to a thickness) of the first transparent member 23. As shown in FIG. 15B, when the blowers 91 blow air to the first transparent member 23, the temperature difference between a center part and a circumferential part in the first transparent member 23 is decreased. It may be considered that a lower surface (outside of the culture container) of the first transparent member 23 is cooled by blowing air, and a direction of a heat flow is changed to a thickness direction.

Thus, in the culture observation apparatus 90 according to the seventh embodiment, it is possible to uniform the heat generation temperature of the first transparent member 23, i.e., to uniform the culture environment of each well 31 of the well plate 30.

(Eighth Embodiment)
[Configuration of Culture Observation Apparatus]

Figure 16:
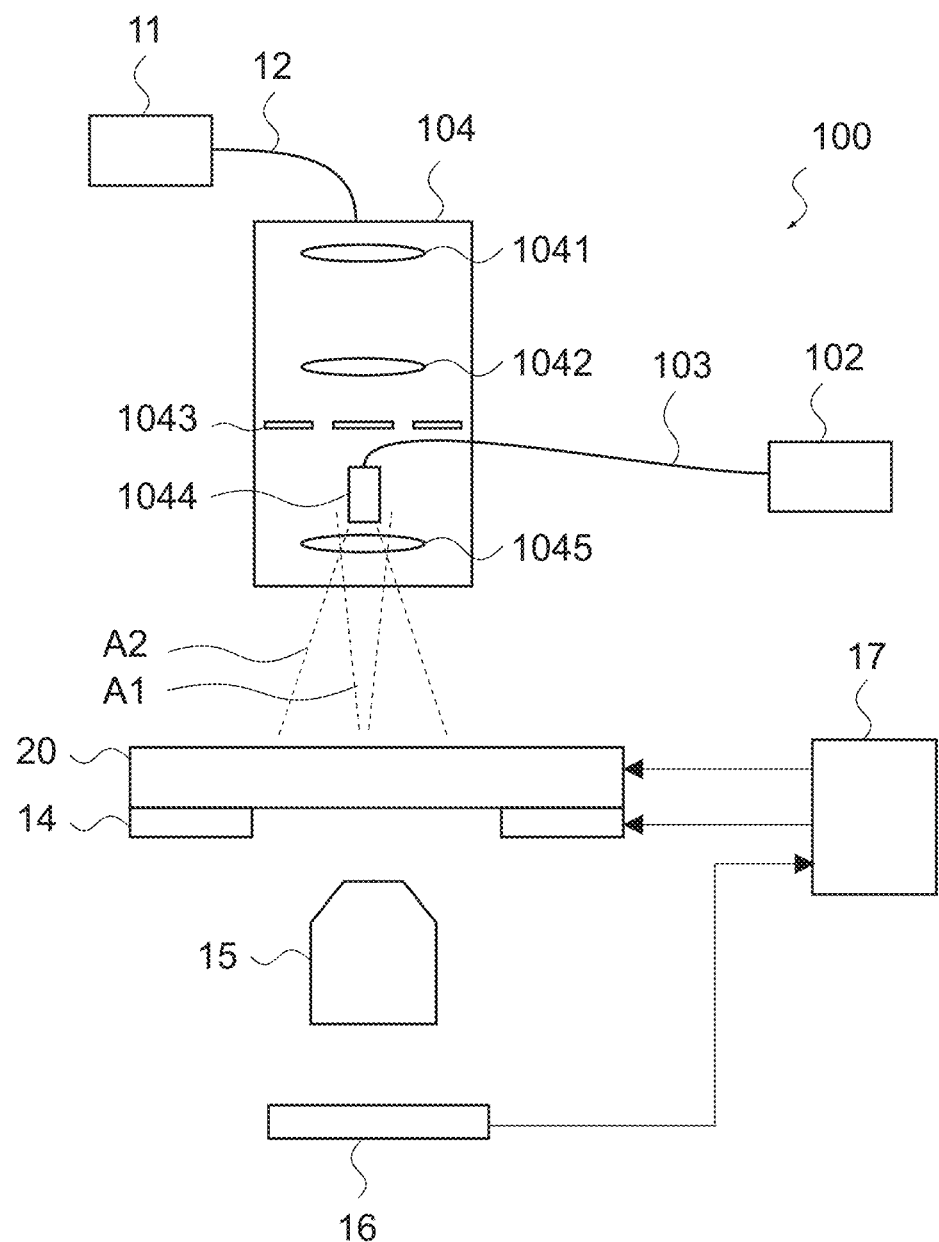
FIG. 16 is a schematic diagram of a culture observation apparatus according to an eighth embodiment.

A culture observation apparatus according to an eighth embodiment will be described. FIG. 16 is a schematic diagram of a culture observation apparatus 100 according to the eighth embodiment. As shown in FIG. 16, the culture observation apparatus 100 includes the illumination light source 11, the optical fibers 12, the stage 14, the microscope optical system 15, the image capture sensor 16 and the control unit 17 similar to the culture observation apparatus 1 according to the first embodiment, but includes a different illumination optical system 13. The culture observation apparatus 100 further includes an infrared light source 102 and optical fibers 103. To the culture observation apparatus 100, any of the culture containers shown in the first to sixth embodiments may be set. Here, the culture container 20 according to the first embodiment will be described as an example.

The infrared light source 102 generates infrared rays. As the infrared light source 102, any light sources such as a halogen lamp can be used. The optical fibers 103 transmit the infrared rays irradiated from the infrared light source 102 to an illumination optical system 104.

The illumination optical system 104 can have a first lens 1041, a second lens 1042, a draw ring 1043, an infrared illumination unit 1044 and a condenser lens 1045. The first and second lenses 1041 and 1042, the draw ring 1043 and the condenser lens 1045 are an optical system for illuminating the illuminated light generated by the illumination light source 11 and transmitted by the optical fibers 12 to the object to be observed similar to the first embodiment.

The infrared illumination unit 1044 is an optical system that is connected to the optical fibers 103, and illuminates the infrared rays transmitted from the optical fibers 103 to the second transparent member 22 of the culture container 20. The infrared illumination unit 1044 can be configured by a kaleidoscope or a fly array lens.

Figure 17:
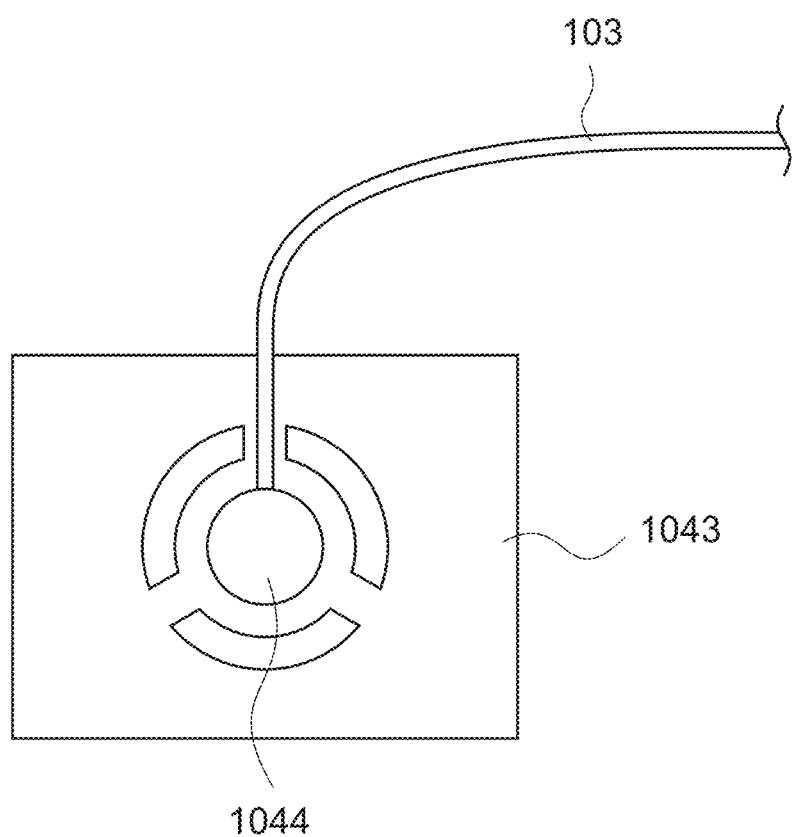
FIG. 17 is a schematic diagram showing a configuration of an infrared irradiation unit to a draw ring in the culture observation apparatus.

The infrared illumination unit 1044 can be disposed to have a predetermined positional relationship with the draw ring 1043. FIG. 17 is a schematic diagram showing a configuration of an infrared irradiation unit 1044 to the draw ring 1043. As shown in FIG. 17, the infrared illumination unit 1044 can be disposed at an inner periphery of slits of the draw ring 1043 and at the side of the object to be observed (the culture container 20) of the draw ring 1043.

By such a configuration, the culture container 20 is irradiated with the illumination light for capturing the phase difference image and infrared rays from the illumination optical system 104. The above-described positional relationship between the infrared illumination unit 1044 and the draw ring 1043 as shown in FIG. 16 allows light axes of the illuminated light A1 and the infrared rays A2 to be the same.

When the second transparent member 22 (see FIG. 5) of the culture container 20 is made of an infrared absorbing material, the second transparent member 22 can generate heat by the infrared rays irradiated from the infrared illumination unit 1044. In this way, when the culture container 20 is open, the second transparent member 22 can also heat the culture space together with the first transparent member 23, thereby keeping the culture environment easily. By adjusting the distance between the lenses in the illumination optical system 104, an intensity distribution of the illuminated light on the second transparent member 22 can be adjusted, thereby adjusting the temperature distribution.

The culture observation apparatus 100 according to the eighth embodiment may have a blower for blowing air to the first transparent member 23 similar to the seventh embodiment. By the blower, the heat generation temperature of the first transparent member 23 can be uniform, and the culture environment can also be uniform.

(Ninth Embodiment)

[Configuration of Culture Observation Apparatus]

A culture observation apparatus according to a ninth embodiment will be described. A culture observation apparatus 110 according to the ninth embodiment includes a control unit 1101 having the following configurations: The configurations other than the control unit 1101 in the culture observation apparatus 110 are similar to those of the culture observation apparatus 1 according to the first embodiment (see FIG. 1). To the culture observation apparatus 110, any of the culture containers shown in the first to sixth embodiments may be set. Here, the culture container 20 according to the first embodiment will be described as an example.

Figure 18:
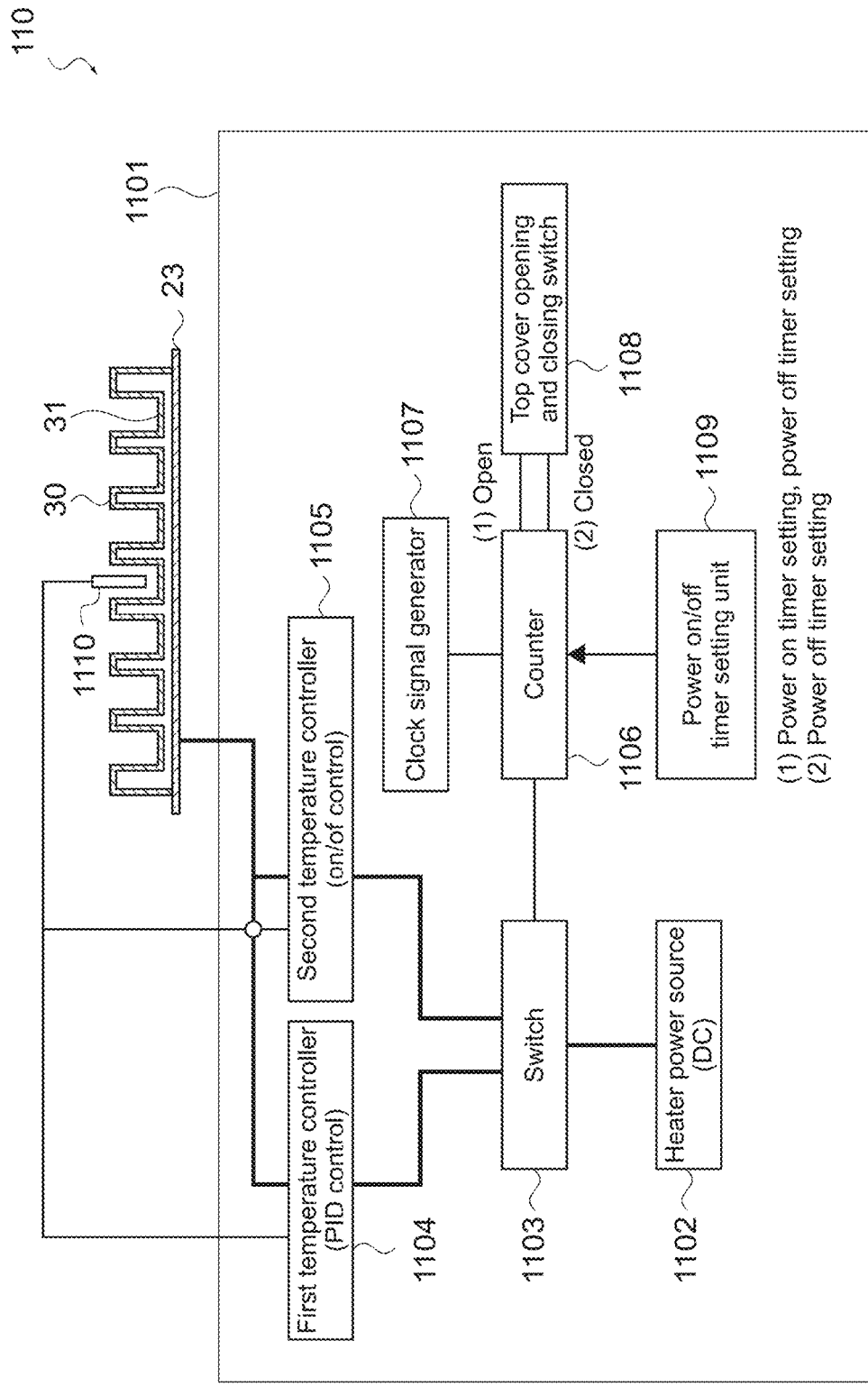
FIG. 18 is a schematic diagram showing a functional configuration of a control unit of the culture observation apparatus according to a ninth embodiment.

FIG. 18 is a schematic diagram showing a functional configuration of a control unit 1101. As shown in FIG. 18, the control unit 1101 has a heater power source 1102, a switch 1103, a first temperature controller 1104, a second temperature controller 1105, a counter 1106, a clock signal generator 1107, a top cover opening and closing switch 1108, and a power on/off timer setting unit 1109. On the culture container 20, a temperature sensor 1110 for measuring a temperature of the wells 31 is disposed. The second temperature controller 1105 may be a volume control knob disposed on the first temperature controller 1104.

Figure 19:
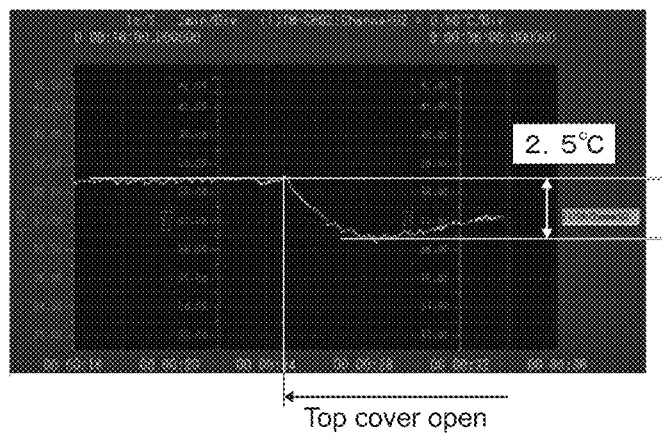
FIG. 19 is a graph showing a measured temperature before and after opening of a cover of the culture observation apparatus.
Figure 20:
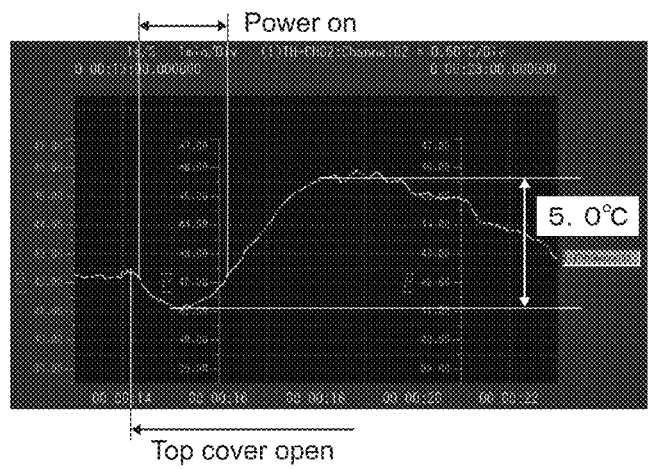
FIG. 20 is a graph showing a measured temperature before and after opening of a cover of the culture observation apparatus.
Figure 21:
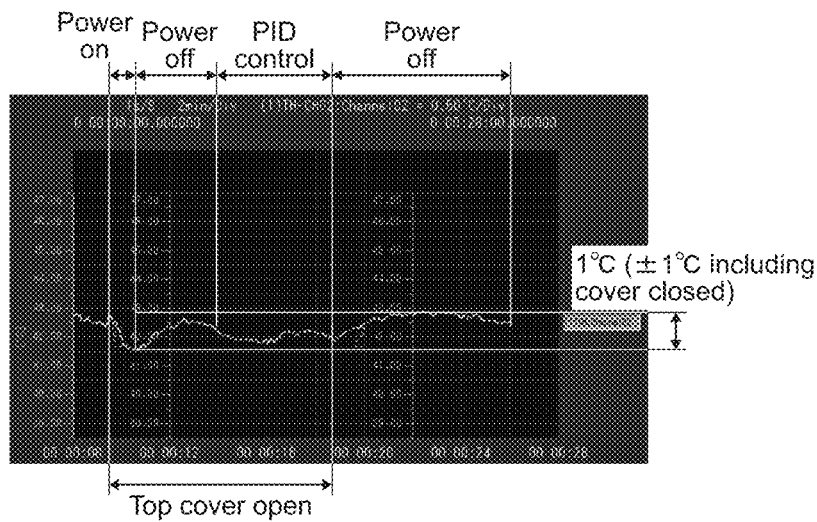
FIG. 21 is a graph showing a measured temperature before and after opening of a cover of the culture observation apparatus.

FIGS. 19 to 21 are each a graph showing a measured temperature by the temperature sensor 1110 before and after opening of the top cover (a cover 211). FIG. 19 shows a temperature change accompanied by an opening of the top cover when the liquid L is not injected into the culture container 20. The temperature decrease amount at this time was 2.5° C. This is because the temperature decrease caused by the culture vaporization cannot be prevented even if a PID (Proportional/Integra/Differential) control by the first temperature controller 1104 of the first transparent member 23 is set to a maximum (fastest).

FIG. 20 shows the result obtained by a temperature controller in the related art according to the logic as shown in FIG. 18. Here, the temperature control is performed by the PID control by the first temperature controller 1104 except when the top cover is open, and is switched to a rapid-response on/off control by the second temperature controller 1105.

However, if it is left as it is, the apparatus may be powered on until it reaches the control temperature as shown in FIG. 20. Even if a heat input is ended, the temperature may continue to rise due to after heat. FIG. 21 shows the result of the temperature control by powering on the heater power source 1102 and then powering off it after a certain time is elapsed. This improves the temperature decrease amount as low as about 1° C. (As the PID control of the first temperature controller 1104 has no problem when the top cover is not open/closed, it is switched to the first temperature controller 1104 after the temperature is stabilized). Although the second temperature controller 1105 is used for controlling the temperature, it may be "an output controller" of the heater power source 1101, which does not impair the function.

After the top cover is closed, the temperature is increased and another power off time ((2) in FIG. 18) is therefore set. In order to decrease the temperature increase amount, the heater power source 1102 of the second transparent member 22 may be turned off at the same time. The time is controlled by a clock signal generated from the clock signal generator 1107 and by a counting using the counter 1106.

The top cover opening and closing switch 1108 that generates a signal by opening and closing the top cover may be replaced with an electrical switch. For example, the clock signal generator 1107 may be a crystal oscillator, and the counter 1106 may be a counter circuit. The switch 1103 switches the first temperature controller 1104 to the second temperature controller 1105. In general, a relay circuit, a multiplexer, or the like may be used.

As described above, according to the ninth embodiment, the controller 1101 switches the PID control to the on/off control, or vice versa, to control the heating temperature of the first transparent member 23. It is thus possible to decrease a change in the culture environment when the cover 211 is open.

EXAMPLES

Figure 22:
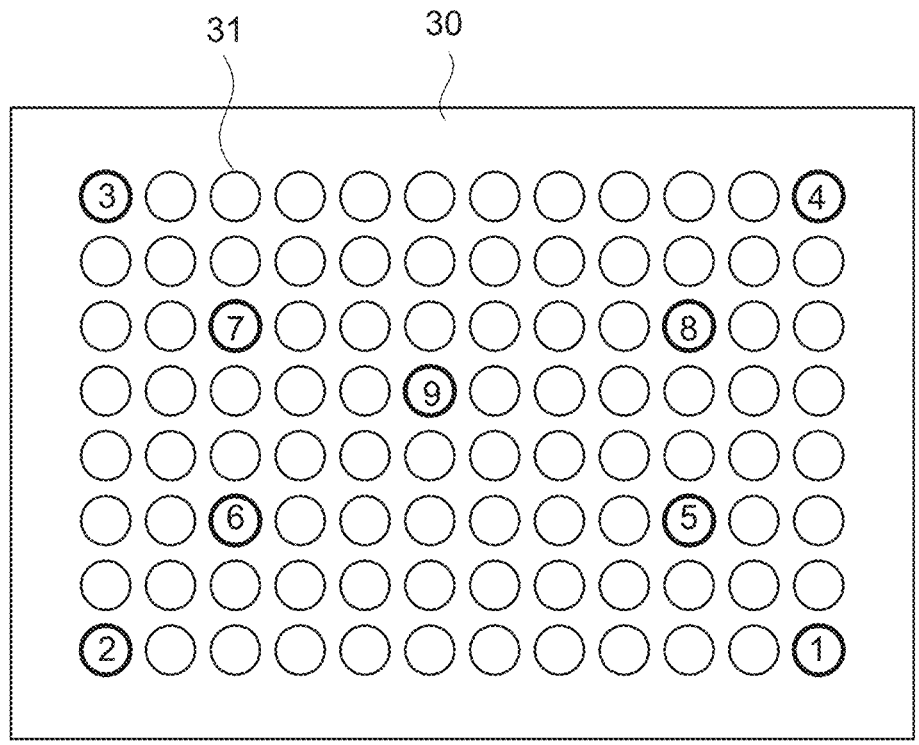
FIG. 22 is a schematic diagram showing wells and temperature sensors disposed on the wells according to embodiments.
Figure 23:
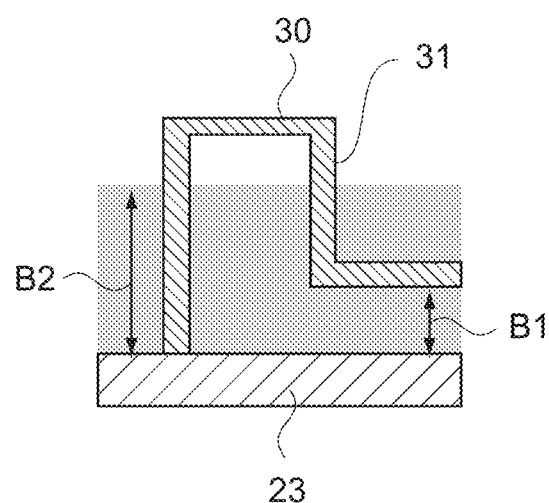
FIG. 23 is a schematic diagram showing a liquid level according to embodiments.

Examples of the above-described respective embodiments will be described. In the measurements below, the temperature sensors were placed in the specified wells 31 of the well plate 30 to measure the temperature of water (alternative to the culture media) injected into the wells 31. FIG. 22 shows the wells 31 in which the temperature sensors are placed and numbers corresponding to the temperature sensors placed on the wells 31. As shown in FIG. 23, a distance between the bottom surface of the well 31 and the first transparent member 23 is denoted as B1, and the liquid level (from the first transparent member 23) of the liquid L is denoted as B2.

Figure 26:
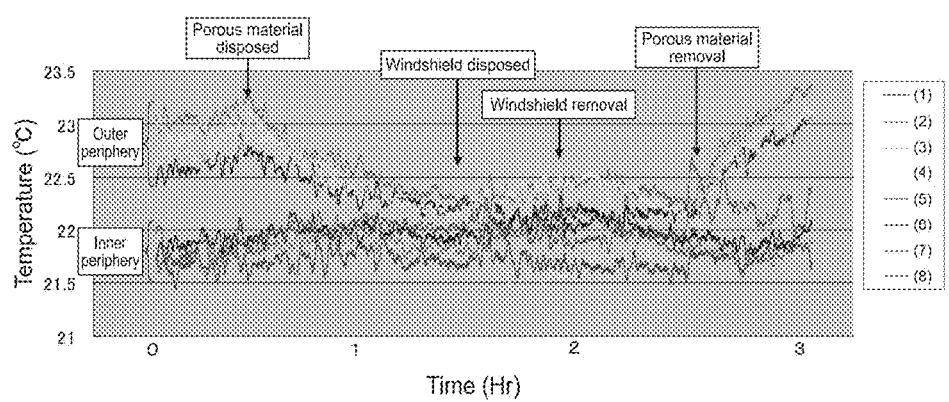
FIG. 26 is a graph showing measured values according to embodiments.

FIGS. 24 and 25 are each a table showing the measured values measured by the temperature sensor under respective conditions (see FIG. 22). FIG. 26 is a graph showing the measured values measured by the temperature sensor when the porous material is disposed. The measurements 1, 2, 3 reveal that a temperature irregularity is better as the distance B1 becomes shorter. In the measurement 1, the temperature of the outer periphery is low, which tends to directly reflect the temperature distribution of the first transparent material 23. By providing the side heater 41 (see the second embodiment), it is possible to prevent the temperature of the outer periphery from decreasing lower than the inner periphery, as shown in the measurement result 1-(1).

In contrast, in the measurements 2 and 3, the temperature distribution of the first transparent member 23 is indirectly shown. The temperature of the outer periphery of the well plate is higher than the inner periphery of the well plate. Also, this applies to the measurements 4 and 5 where no liquid L is injected, and the reason thereof will be described later. In the measurements 4 and 5, the temperature irregularity is relatively small, but the temperature decrease amount is great (about 1.5° C. in the measurement 4 and about 2.5° C. in the measurement 5). On the other hand, when the well plate 30 having the skirt 32 (see FIG. 3) is used, i.e., the skirt 32 is raised using the well plate support member 51 as shown in FIG. 9, FIG. 25 shows temperature measurement results.

In the measurement 6, the temperature irregularity has a direction dependency, but, in the measurement 7, the temperature irregularity becomes better. The temperature irregularity is due to the irregular thermal conduction caused by a contact of the skirt 32 with the first transparent member 23. It was confirmed that the temperature irregularity was improved by the well plate support member 51. Hence, in the measurement 8 where the liquid L is directly injected, the temperature irregularity gets worse.

When the liquid L is injected while the skirt 32 is raised, an optical distance between the microscope optical system 15 and the object to be observed is too great and an optical aberration forms an issue. In the measurements 9 and 10, the side heater 41 was used, respectively. In the measurement 10, the temperature irregularity was better when the side heater 41 was at 37° C.

The reason that the outer periphery of the well plate 30 had high temperature in the measurements 2, 3, 4 and 5 is vaporization by surrounding environment humidity. By disposing the porous member 61 (see the fourth embodiment) containing and being saturated with the liquid L around the outer periphery of the well plate 30 as shown in FIG. 10, it is confirmed that the temperature of the outer periphery of the well plate 30 is coincided with the temperature of the inner periphery of the well plate 30 as shown in FIG. 26 (water having the same temperature as the environment substitutes for the culture media).

The present disclosure may have the following configurations.

(1) A culture container, including:
a first transparent member being capable of keeping a predetermined temperature;
a second transparent member facing to the first transparent member;
a housing member to which the first transparent member and the second transparent member are adhered forming a culture space being capable of housing a well plate together with the first transparent member and the second transparent member; and
a sealing member for sealing a liquid injected into the culture space between the first transparent member and the housing member.

(2) The culture container according to (1) above, further including:
a porous member for coating a liquid level of the liquid injected into the culture space.

(3) The culture container according to (1) or (2) above, further including:
an antiscattering member adhered to the porous member for coating a gap between the well plate housed in the culture space and the porous member.

(4) The culture container according to any one of (1) to (3) above, in which
a notch is formed on the first transparent member that forms a gap between the first transparent member and the well plate disposed on the first transparent member.

(5) The culture container according to any one of (1) to (4) above, further including:
a support member made of a thermal insulation material for supporting the well plate housed in the culture space.

(6) The culture container according to any one of (1) to (5) above, in which
the first transparent member includes a transparent plate having an optical transparency, a pair of electrodes formed on the transparent plate per segment of the transparent plate, and a transparent conductive film formed on the transparent plate and connected to the pair of electrodes per segment of the transparent plate.

(7) A culture observation apparatus, including:
a culture container including a first transparent member being capable of keeping a predetermined temperature, a second transparent member facing to the first transparent member, a housing member to which the first transparent member and the second transparent member are adhered forming a culture space being capable of housing a well plate together with the first transparent member and the second transparent member and a sealing member for sealing a liquid injected into the culture space between the first transparent member and the housing member;
an illumination optical system for irradiating the culture container with an illumination light; and
a microscope optical system for generating a phase difference image from the illumination light irradiated from the illumination optical system and transmitted through the culture container.

(8) The culture observation apparatus according to (7) above, further including:
a blower blowing air to the first transparent member.

(9) The culture observation apparatus according to (7) or (8) above, in which
the first transparent member includes an infrared absorbing material, and the illumination optical system irradiates the second transparent member with the illuminated light and infrared rays.

(10) The culture observation apparatus according to any one of (7) to (9) above, in which
the illumination optical system includes a draw ring having a ring-shaped slit and an infrared illumination unit disposed at the culture container side of the ring-shaped slit and at an inner periphery of the ring-shaped slit.

(11) A culture observation method, including:
preparing a culture container including a first transparent member being capable of keeping a predetermined temperature, a second transparent member facing to the first transparent member, a housing member to which the first transparent member and the second transparent member are adhered forming a culture space being capable of housing a well plate together with the first transparent member and the second transparent member and a sealing member for sealing a liquid injected into the culture space between the first transparent member and the housing member;
housing the well plate in which an object to be observed is housed into the culture space;
injecting a liquid into the culture space; and
keeping the culture space to a culture environment of the object to be observed.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A culture container, comprising:
a first transparent member configured to be controlled by a controller that at least substantially maintains the first transparent member at a predetermined temperature;
a second transparent member facing the first transparent member;
a housing member to which the first transparent member and the second transparent member are adhered, the housing member forming a culture space together with the first transparent member and the second transparent member;
a well plate disposed in the culture space and including a plurality of wells;
a sealing member for sealing a liquid injected into the culture space between the first transparent member and the housing member, wherein the well plate is disposed in the culture space such that the liquid surrounds bottom surfaces of the wells and at least portions of side surfaces of the wells; and
a support member made of a thermal insulation material and provided in the housing member in a state of noncontact with the first and second transparent members,
wherein the support member is configured to support the well plate in the culture space in a state of noncontact with the first transparent member, the second transparent member and the housing member, and
wherein the well plate includes a skirt disposed around an outer perimeter of the well plate, and the support member is configured to support the well plate such that only a bottom surface of the skirt contacts the support member.

2. The culture container according to claim 1, further comprising:
an antiscattering member adhered to the porous member for coating a gap between the well plate housed in the culture space and the porous member.

3. The culture container according to claim 1, wherein
a notch is formed on the first transparent member that forms a gap between the first transparent member and the well plate disposed on the first transparent member, wherein the notch forms a liquid flow path to an interior space defined by the well plate and the first transparent member.

4. The culture container according to claim 1, wherein
the first transparent member includes a transparent plate having an optical transparency, a pair of electrodes formed on the transparent plate per segment of the transparent plate, and a transparent conductive film formed on the transparent plate and connected to the pair of electrodes per segment of the transparent plate.

5. The culture container according to claim 1, further comprising a waterproof member provided on the first transparent member.

6. The culture container according to claim 1, wherein the skirt has a height higher than a depth of the wells.

7. The culture container according to claim 1, wherein the first transparent member is configured as a first heater, the culture container further comprising a second heater disposed in the housing member around an outer perimeter of the well plate.

8. A culture observation apparatus, comprising:
a culture container including a first transparent member configured to be controlled by a controller that at least substantially maintains the first transparent member at a predetermined temperature, a second transparent member facing to the first transparent member, a housing member to which the first transparent member and the second transparent member are adhered and the housing member forming a culture space together with the first transparent member and the second transparent member, a well plate disposed in the culture space and including a plurality of wells, and a sealing member for sealing a liquid injected into the culture space between the first transparent member and the housing member, wherein the well plate is disposed in the culture spaces such that the liquid surrounds bottoms of the wells and at least portions of sides of the well;
an illumination optical system for irradiating the culture container with an illumination light;
a microscope optical system for generating a phase difference image from the illumination light irradiated from the illumination optical system and transmitted through the culture container; and
a support member made of a thermal insulation material and provided in the housing member in a state of noncontact with the first and second transparent members,
wherein the support member is configured to support the well plate in the culture space in a state of noncontact with the first transparent member, the second transparent member and the housing member, and
wherein the well plate includes a skirt disposed around an outer perimeter of the well plate, and the support member is configured to support the well plate such that only a bottom surface of the skirt contacts the support member.

9. The culture observation apparatus according to claim 8, further comprising:
a blower blowing air to the first transparent member.

10. The culture observation apparatus according to claim 8, wherein
the first transparent member includes an infrared absorbing material, and
the illumination optical system is configured to irradiate the second transparent member with an infrared ray and the illumination light.

11. The culture observation apparatus according to claim 10, wherein
the illumination optical system includes a draw ring having a ring-shaped slit and an infrared illumination unit disposed at the culture container side of the ring-shaped slit and at an inner periphery of the ring-shaped slit.

12. The culture observation apparatus according to claim 8, further comprising a waterproof member provided on the first transparent member.

\* \* \* \* \*